United States Patent [19]

Fujita et al.

[11] 4,008,124
[45] Feb. 15, 1977

[54] PROCESS FOR THE ISOMERIZATION OF GLUCOSE INTO FRUCTOSE

[75] Inventors: Yoshimasa Fujita, Tokyo; Akiyoshi Matsumoto, Hino; Hachiro Ishikawa, Chofu; Tadashi Hishida; Hideo Kato, both of Tokyo; Hiroshi Takamisawa, Yokohama, all of Japan

[73] Assignees: Mitsubishi Chemical Industries Ltd.; Seikagaku Kogyo Co., Ltd., both of Tokyo, Japan

[22] Filed: June 20, 1975

[21] Appl. No.: 588,823

[30] Foreign Application Priority Data

June 26, 1974 Japan .............................. 49-73125

[52] U.S. Cl. .............................. 195/31 F; 195/62; 195/68; 195/DIG. 11
[51] Int. Cl.² ...................................... C12D 13/02
[58] Field of Search ............ 195/31 F, 68, DIG. 11, 195/63, 114, 66 R, 62

[56] References Cited

UNITED STATES PATENTS

| | | |
|---|---|---|
| 3,645,852 | 2/1972 | Axen et al. ............. 195/DIG. 11 X |
| 3,705,084 | 12/1972 | Reynolds ......................... 195/68 X |
| 3,708,397 | 1/1973 | Sipos ............................... 195/31 F |
| 3,770,589 | 11/1973 | Heady et al. ..................... 195/66 R |
| 3,788,945 | 1/1974 | Thompson et al. ............. 195/31 F |
| 3,868,304 | 2/1975 | Messing ........................... 195/31 F |

OTHER PUBLICATIONS

Tz-Yuan et al., "D-Xylose Isomerase of Streptomyces-griseus," *Acta Biochimica et Biophysica Siwca*, vol. 14, No. 3, pp. 342–350 (1964).

Patterson, "Preparation of Cross Linked Polystyrenes and Their Derivatives for Use as Solid Supports or Insoluble Reagents", *Biochemical Aspects of Reactions on Solid Supports*, Stark ed., Academic Press, N.Y. and London, pp. 189–213 (1971).

Yoshimura et al., "Studies on D-Glucose Isomerising Activity of D–Xylose Grown Cells from Bacillus Coagulans Strain HN–68 Part I, Description of the Strain and Conditions for the Formation of the Activity," *Agr. Biol. Chem.*, vol. 30, No. 10, pp. 1015–1023 (1966).

Stranberg et al., "Free and Immobilized Glucose Isomerase from *Streptomyces phaechromogenes*", *Applied Microbiology*, vol. 21, No. 4, pp. 588–593 (1971).

Primary Examiner—A. Louis Monacell
Assistant Examiner—Thomas G. Wiseman
Attorney, Agent, or Firm—Oblon, Fisher, Spivak, McClelland & Maier

[57] ABSTRACT

There is disclosed a process for isomerization of glucose into fructose which comprises contacting an aqueous glucose solution with glucose isomerase in the presence of iron ion and magnesium ion, said glucose isomerase being in the form of insolubilized glucose isomerase adsorbed on a carrier.

12 Claims, No Drawings

PROCESS FOR THE ISOMERIZATION OF GLUCOSE INTO FRUCTOSE

This invention relates to a process for producing fructose which comprises converting glucose into fructose by glucose isomerase, in more particular, to an isomerization of glucose into fructose by glucose isomerase in which there is present iron ion together with magnesium ion to prevent deactivation of glucose isomerase.

It has already been known that glucose isomerase is an enzyme capable of converting glucose into fructose and vice versa and is used for producing fructose from glucose.

Such glucose isomerase has been observed in various microorganisms examples of which include, for example, bacteria such as Pseudomonas, Bacillus and Lacto bacillus, actinomycetes such as *Streptomyces phaeochromogenus*, *Streptomyces fradie*, *Streptomyces roseochromogenus*, *Streptomyces olivaceus*, *Streptomyces californicus*, *Streptomyces vinaceus* and *Streptomyces albus* and yeasts. For practical purposes, it is preferred to use glucose isomerase isolated from Streptomyces in an insolubilized form which is obtained either by subjecting microbial cells containing glucose isomerase to heat treatment to effect intracellular fixation or by attaching glucose isomerase isolated from the cells to a carrier by adsorption ion-exchange, formation of a covalent bond or inclusion processing. For example, reference is made to Chemical Abstracts Vol. 69, 64824 d (1968) Tsumura et al.; U.S. Pat. No. 3,788,945; Applied Microbiology, April 1971, p. 588–593, G. W. Strandberg et al.; and Biotechnology and Bioengineering Vol. XIV, p. 509–513 (1972), G. W. Strandberg et al.

Almost all of the glucose isomerases found in microbial cells require metal ion which may vary depending upon the origin of isomerase. It has been known that glucose isomerase found in Streptomyces requires magnesium ion and that activity and resistance to heat are enhanced in the presence of additional cobaltous ion [refer to N. Tsumura et al. Agr. Biol. Chem. Vol. 29, 1126 (1965) and T. Takasaki, Agr. Biol. Chem. Vol. 30, p. 1249 (1966)].

In this connection, in commercial practice of fructose production from glucose, magnesium and cobaltous ions have been present in the reaction mixture; however, such process is not recommendable since various heavy metal ions including cobaltous ion are not allowed as additives to foodstuff in many countries and therefore the use of such cobaltous ion in the production of fructose should be avoided.

Thus, we have conducted intensive studies in order to find an additive by which activity of glucose isomerase is maintained for a long time without using cobaltous ion and we have found that such object is accomplished by addition of a trace amount of water soluble iron salt together with magnesium salt to a glucose isomerization mixture.

Accordingly, an object of this invention lies in effectively utilizing glucose isomerase in the conversion of glucose into fructose and this object is accomplished according to this invention in which either a trace amount of iron ion is added to the reaction mixture of glucose isomerization or glucose isomerase is previously treated with an aqueous solution of a water soluble iron salt.

Now, this invention will be explained in detail. The examples of iron ion source which may be employed according to this invention include water soluble iron salts, for example, an inorganic iron salt, such as iron sulfate, iron chloride and iron nitrate and an organic iron salt, such as iron tartarate. However, attention should be given to some organic iron salts, which are water soluble, because, if base anion coordinates strongly to iron, the performance of iron ion is diminished by virtue of a so-called masking effect.

Further, among inorganic salts, iron phosphates are inconvenient since they have low solubility in water and give an insoluble precipitate. Ferric chloride, ferrous sulfate, iron lactates, iron citrates and ammonium iron citrates which are allowed as additives to foodstuff according to the Foodstuff Sanitation Law of Japan are exemplified as water soluble iron salt of this invention. As appears from the following Examples, the water soluble iron salt may be either bivalent or trivalent.

Although the behavior and mechanism of iron ion according to this invention have not yet been made clear, it is believed, without being bound by any theories, that, if iron ion is present together with magnesium ion in the reaction mixture, the iron ion attaches to enzyme to form a certain complex which resists deactivation of enzyme caused by chemical and/or heat action. Thus, it is possible to subject to glucose isomerase a pretreatment with an aqueous iron salt solution and then the intended effect is achieved without addition of iron salt so far as iron ion is present near the isomerase. However, it is preferable in such case to add iron salt to the reaction mixture thereby maintaining a constant level of the concentration of iron ion in the reaction mixture, because iron ion which has been attached to glucose isomerase to form such complex dissociates later on and is removed from the reaction mixture in conjunction with the product, especially in a continuous process.

The examples of water soluble iron salt which may be used in this invention include ferrous sulfate, ferric sulfate, ferrous chloride, ferric chloride, ammonium ferric sulfate, ammonium ferrous sulfate and a mixture thereof.

The concentration of iron ion to be maintained in the reaction mixture ranges in general from 0.005 to 5 m. Mole/lit. and preferably 0.02 to 0.5 m. Mole/lit.

Examples of water soluble magnesium salt which may be used together with the iron salt in this invention include magnesium sulfate, magnesium chloride, magnesium sulfite, magnesium carbonate and a mixture thereof. The concentration of magnesium salt ranges in general from 2 to 20 m. Mole/lit.

The isomerization of glucose into fructose according to this invention is suitable for continuous process in which an aqueous glucose solution is contacted continuously with insolubilized glucose isomerase to obtain fructose. Especially, this invention is adaptable for a continuous process using insolubilized glucose isomerase in which an aqueous glucose solution is passed through a column into which glucose isomerase adsorbed on a carrier is packed to effect conversion of glucose into fructose.

The carrier suitable for the purpose of insolubilizing glucose isomerase includes:

1. a macroporous anion exchange resin the matrix of which is styrene-divinyl copolymer and anion exchange group is a quarternary ammonium type and details thereof are fully described in our copending application of U.S. Ser. No. 561,837 filed on Mar. 25, 1975 the disclosures of which are referred to in this application, and 2. a cyanogen halide derivative of cross-linked agar in particle form.

The latter is produced by treating agar with a cross-linking agent such as epichlorohydrin under alkaline condition to introduce cross-linkages followed by heating at a high temperature and washing with hot water to remove hot water-soluble materials, then treating the cross-linked agar with an aqueous solution of cyanogen halide such as cyanogen bromide under alkaline condition.

It has been observed that, in practice according to this invention, the activity of such insolubilized isomerase is maintained for a long period and, thus, the isomerization reaction of glucose to fructose is satisfactory for use on a commercial basis.

An aqueous glucose solution is conveniently subjected to a continuous process according to this invention at a pH ranging from 5.5 to 9, a concentration of 20 to 70% by weight and a temperature of 40° to 80° C and such solution is passed through such column at a space velocity of 0.1 to 20 $hr^{-1}$.

This invention will further be explained in detail by way of Example. However, it should be understood that such Examples are given only for illustration and this invention is in no way limited by them.

EXAMPLE 1

Glucose isomerase was extracted by a conventional ultrasonic treatment from "Glucose Isomerase NAGASE" which consisted of cells of strain belonging to *Streptomyces phaeochromogenes*, intracellularly fixed by heat treatment and available from Nagase Sangyo Kabushiki Kaisha, Osaka, Japan.

The activity titer, which is defined hereinafter, of such extract was 200 U/ml.

Then, an insolubilized glucose isomerase was prepared by mixing 75 ml of such extract with 15 ml in wet state of a macroporous strong basic anion exchange resin (Diaion HPA available from Mitsubishi Chemical Industries, Limited, and the matrix of which was styrenedivinyl benzene copolymer and the ion exchange group of which was a quarternary ammonium group) at room temperature for six hours to effect adsorption of the isomerase on the anion exchange resin, the degree of adsorption being measured as more than 99%. The insolubilized glucose isomerase thus prepared was packed into a jacketed column of an 8 mm inner diameter.

A 3 Mole aqueous glucose solution containing 5 m. Mole of magnesium sulfate and 1 m. Mole of ferrous sulfate, as ion concentrations, respectively, was passed through such column maintained at a temperature of 67° C to effect continuous isomerization, while passing warmed water through into the jacket.

The degrees of activity retention defined hereinbelow after 10 and 20 days are given in Table 1.

EXAMPLES 2 to 6

Procedures similar to those of Example 1 were repeated excepting that instead of ferrous sulfate various metal salts at given concentrations listed in Table 1 were employed. The degrees of activity retention of the glucose isomerase after 10 and 20 days are also shown in Table 1 from which superior results derived from the addition of iron salts to other salts are proved in respect that prolonged isomerase activity is maintained.

Table 1

| Example No. | Compound | Concentration of the ion (m. Mole/lit.) | Degree of activity retention (%) 10 days | 20 days |
|---|---|---|---|---|
| 1 | Ferrous chloride | 1.0 | 70 | 45 |
| 2 | Ferric chloride | 0.5 | 62 | 37 |
| 3 | Iron tartarate | 1.0 | 68 | 40 |
| 4 | — | — | 33 | 11 |
| 5 | Cobaltous chloride | 1.0 | 55 | 25 |
| 6 | Calcium chloride | 1.0 | 30 | 13 |

EXAMPLES 7 to 13

In these Examples, the procedures of Example 1 were followed but the isomerizations were carried out at a temperature of 72° C using ferric sulfate in the various concentrations given in Table 2.

The degrees of activity retention after 7 and 13 days are also shown in Table 2.

Lower value in decrease of the activity is observed at a concentration of ranging from 0.02 to 0.5 m. Mole/lit. of iron ion.

Table 2

| Example No. | Concentration of iron ion (m. Mole/lit.) | Degree of activity retention (%) 7 days | 13 days |
|---|---|---|---|
| 7 | 0 | 13 | 5 |
| 8 | 0.02 | 40 | 22 |
| 9 | 0.05 | 52 | 35 |
| 10 | 0.1 | 62 | 49 |
| 11 | 0.25 | 50 | 33 |
| 12 | 0.5 | 38 | 11 |
| 13 | 3.0 | 26 | 9 |

EXAMPLES 14 to 16

Glucose isomerase employed was extracted from the culture medium incubated *Streptomyces albus* YT No. 5 which had been deposited with The Fermentation Research Institute, Japan (deposit No.: FERM P-463). The isomerase was insolubilized according to the procedures of Example 1 and used in continuous isomerizations as in Examples 1, 4 and 5. The degrees of activity retention after 7 and 13 days are given in Table 3.

Table 3

| Example No. | Compound | Concentration of ion (m. Mole/lit.) | Degree of activity retention (%) 7 days | 13 days |
|---|---|---|---|---|
| 14 | Ferrous sulfate | 1.0 | 75 | 60 |
| 15 | — | — | 40 | 25 |
| 16 | Cobaltous chloride | 1.0 | 62 | 49 |

EXAMPLES 17 to 19

Preparation of cross-linked agar particles

One liter of 4% agar particle, Sepharose 4B available from Pharmacia Fine Chemicals, Sweden, was thoroughly mixed with one liter of an aqueous sodium hydroxide solution (1 Mole/lit.) at room temperature. Thirty milliliter of epichlorohydrin was added to the above mixture while maintaining at 60° C on a water bath and thoroughly shaken for 2 hours whereby cross-linking reaction was effected.

Then, the reaction mass was heated in an autoclave at a temperature of 120° C, under a pressure of 2 atm. for 2 hours, the hot mass was washed with hot water at 90° C to remove hot water-soluble material and allowed to cool on standing to obtain cross-linked agar particles.

Activation of cross-linked agar particles

The cross-linked agar particles were subjected to vacuum filtration to remove excess water and allowed to cool to 4° C. To a mixture of 50 g of the particles thus obtained and 80 ml of a 2% aqueous cyanogen bromide solution was added dropwise a 2 N aqueous sodium hydroxide at such a rate that the solution was maintained at a pH of 11 ± 0.5 thereby activating the cross-linked agar.

When absorption of alkali stopped (this being detected by increase of the pH value), the addition of the alkali stopped, and the reaction mass was subjected to vacuum filtration and washed with water to obtain activated and cross-linked agar particles.

Insolubilization of glucose isomerase

A mixture of 50 g of the activated particles thus obtained and the glucose isomerase extract of Example 1 and having an activity titer of 25000 U was maintained at a temperature of 4° C for 18 hours to effect the adsorption of the isomerase to the particles thereby obtaining an insolubilized glucose isomerase in particle form.

Isomerization reaction

The insolubilized glucose isomerase above, the activity titer being 4000 U, was packed in a jacketed column (1.5 cm inner diameter and 12 cm length) through which an aqueous glucose solution in a concentration of 3 Mole/lit. and containing various metal ions listed in Table 4 at a rate of 8.5 ml/hr was downwardly passed at a temperature of 67° C to effect continuous isomerization.

Table 4 gives type and concentration of metal ions which are added to the glucose solution and the variation in the amount of fructose produced as time passed.

The degree of activity retention and the activity titer referred to in the specification and the claims are measured as follows.

Degree of activity retention

An aqueous substrate solution containing glucose, magnesium sulfate, cobaltous chloride and phosphate buffer (pH = 7.2) at a concentration of 0.1 Mole/lit., 0.05 Mole/lit., 0.001 Mole/lit. and 0.05 Mole/lit., respectively, is prepared. A predetermined amount of insolubilized glucose isomerases, usually being 1 to 10 ml, after use for a given number of days in the isomerization reaction and before use in the isomerization are added to each 100 ml of the substrate solution and the isomerization is effected at a temperature of 70° C for 60 minutes with gentle agitation.

Then, the isomerase is separated by filtration and the amount of fructose in the filtrate is determined by cystein-carbazole method.

The amount of fructose produced per one milliliter of the insolubilized glucose isomerase is calculated, the values obtained being designated A before and A' after use, respectively. Then, the degree of activity retention is given by the following equation.

$$\frac{A'}{A} \times 100 \ (\%)$$

Activity titer of glucose isomerase extract

A mixture of aqueous solutions of 0.2 ml of 1 M D-glucose 0.2 ml of 0.05 M MgSO$_4$.7H$_2$O and 0.2 ml of 0.5 M phosphate buffer (pH = 7.2) is added to 0.2 ml of glucose isomerase extract and the solution is diluted with water to make 2 ml. The resulting diluted solution is maintained at a temperature of 70° C for 60 minutes to effect isomerization and the reaction is stopped by addition of 2 ml of a 0.5 M aqueous perchloric acid solution. Then the amount of fructose produced is determined by cystein-carbazole method. Then the activity titer expressed by the unit of U is given by the following equation:

$$U = \frac{\text{the amount of fructose produced (mg)}}{\text{the amount of isomerase extract (ml)}}$$

What is claimed is:

1. A process for the isomerization of glucose into fructose by contacting an aqueous glucose solution with glucose isomerase wherein iron ion together with magnesium ion is present in the reaction mixture at concentrations of 0.005 to 5 mm/l and 2 to 20 mm/l, respectively.

2. A process for the isomerization of glucose into fructose according to claim 1, wherein said glucose isomerase is in the form of insolubilized isomerase.

Table 4

| Example No. | Type of metal ions | Concentration of ions (m. Mole/lit.) | Amount of fructose produced after given days. (mg/hr.) | | | | | | | |
|---|---|---|---|---|---|---|---|---|---|---|
| | | | 1 | 2 | 3 | 4 | 5 | 6 | 7 | 8 |
| 17 | Mg$^{++}$ | 5 | 1610 | 1600 | 1600 | 1590 | 1595 | 1580 | 1585 | 1580 |
| | Fe$^{+++}$ | 0.1 | | | | | | | | |
| 18 | Mg$^{++}$ | 5 | 1500 | 1450 | 1462 | 1455 | 1453 | 1450 | 1450 | 1451 |
| | Fe$^{+++}$ | 0.5 | | | | | | | | |
| 19 | Mg$^{++}$ | 5 | 1600 | 1140 | 680 | 540 | 500 | 464 | 415 | 400 |

3. A process for the isomerization of glucose into fructose according to claim 1, wherein said glucose isomerase is in the form of insolubilized isomerase adsorbed on an ion exchanger.

4. A process for the isomerization of glucose into fructose according to claim 1, wherein said glucose isomerase is in the form of insolubilized isomerase adsorbed on a macroporous anion exchange resin.

5. A process for the isomerization of glucose into fructose according to claim 1, wherein said glucose isomerase is in the form of insolubilized isomerase adsorbed on a cyanogen halide derivative of cross-linked agar.

6. A process for the isomerization of glucose into fructose according to claim 1, wherein said glucose isomerase is isolated from the microbial cells of Streptomyces.

7. 17. A process for the isomerization of glucose into fructose according to claim 1, wherein the concentrations of magnesium ion and iron ion are 2 to 20 mM. and 0.02 to 0.5 mM., respectively.

8. A process for the isomerization of glucose into fructose according to claim 1, wherein the iron ion source is ferrous sulfate, ferric sulfate, ferrous chloride, ferric chloride, ammonium ferrous sulfate, ammonium ferric sulfate, iron tartarate or a mixture thereof and the magnesium ion source is magnesium sulfate, magnesium chloride, magnesium sulfite, magnesium carbonate or a mixture thereof.

9. A process for the isomerization of glucose into fructose which comprises passing an aqueous glucose solution containing iron ion at a concentration of 0.005 to 5 mM. and magnesium ion at a concentration of from 2 to 20 mM. through a bed of glucose isomerase isolated from microbial cells of Streptomyces and adsorbed on a macroporous anion exchange resin.

10. A process for the isomerization of glucose into fructose according to claim 9, wherein said macroporous anion exchange resin is a macroporous strong base ion exchange resin the matrix of which comprises a copolymer of styrene-divinyl benzene and ion exchange group is a quarternary ammonium.

11. A process for the isomerization of glucose into fructose according to claim 9, wherein said concentration of iron ion is from 0.02 to 0.5 mM/l.

12. A process for the isomerization of glucose into fructose according to claim 9, wherein the iron ion source present in the aqueous glucose solution is ferrous sulfate, ferric sulfate, ferrous chloride, ferric chloride, iron tartarate, ammonium ferrous sulfate, ammonium ferric sulfate or a mixture thereof.

* * * * *